(12) United States Patent
Laguna et al.

(10) Patent No.: US 7,892,201 B1
(45) Date of Patent: Feb. 22, 2011

(54) BALLOON CATHETER AND METHOD OF MOUNTING SAME

(75) Inventors: Alvaro J. Laguna, Flagstaff, AZ (US); Carey V. Campbell, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 1826 days.

(21) Appl. No.: 09/384,900

(22) Filed: Aug. 27, 1999

(51) Int. Cl.
*A61M 29/00* (2006.01)
(52) U.S. Cl. .................................... 604/96.01
(58) Field of Classification Search ............. 604/96.01, 604/103, 103.05, 103.06, 103.09, 103.11, 604/103.12, 912, 915
See application file for complete search history.

(56) References Cited

U.S. PATENT DOCUMENTS

| | | |
|---|---|---|
| 1,690,995 A | 11/1928 | Pratt |
| 3,953,566 A | 4/1976 | Gore |
| 4,003,382 A | 1/1977 | Dyke |
| 4,106,509 A | 8/1978 | McWhorter |
| 4,187,390 A | 2/1980 | Gore |
| 4,194,041 A | 3/1980 | Gore et al. |
| 4,279,245 A | 7/1981 | Takagi et al. |
| 4,304,010 A | 12/1981 | Mano |
| 4,327,736 A | 5/1982 | Inoue |
| 4,338,942 A | 7/1982 | Fogarty |
| 4,403,612 A | 9/1983 | Fogarty |
| 4,443,511 A | 4/1984 | Worden et al. |
| 4,490,421 A | 12/1984 | Levy |
| 4,573,966 A | 3/1986 | Weikl et al. |
| 4,608,984 A | 9/1986 | Fogarty |
| 4,613,544 A | 9/1986 | Burleigh |
| 4,619,641 A | 10/1986 | Schanzer |
| 4,637,396 A | 1/1987 | Cook |
| 4,650,466 A | 3/1987 | Luther |
| 4,702,252 A | 10/1987 | Brooks et al. |
| 4,706,670 A | 11/1987 | Andersen et al. |
| 4,713,070 A | 12/1987 | Mano |
| 4,737,219 A | 4/1988 | Taller et al. |
| 4,764,560 A | 8/1988 | Mitchell |
| 4,816,339 A | 3/1989 | Tu et al. |
| 4,819,751 A | 4/1989 | Shimada et al. |
| 4,832,688 A | 5/1989 | Sagae et al. |

(Continued)

FOREIGN PATENT DOCUMENTS

EP 372088 6/1990

(Continued)

OTHER PUBLICATIONS

Dillon M E, Silicone and Poly(tetrafluoroethylene) Interpenetrating Polymer Networks. 1994 American Chemical Society.

*Primary Examiner*—Manuel A Mendez
(74) *Attorney, Agent, or Firm*—David J. Johns (57) ABSTRACT

The present invention provides improved methods for forming and mounting a sleeve on a catheter shaft in order to form a distensible balloon catheter. The balloon is formed from a distensible sleeve that is treated to render one or both of its ends essentially non-distensible. The balloon is mounted on the catheter shaft by the non-distensible ends, without compromising the distensible operative portion of the balloon. The balloon may also be mounted using non-distensible tape or similar means to achieve a similar result.

19 Claims, 5 Drawing Sheets

U.S. PATENT DOCUMENTS

| | | | |
|---|---|---|---|
| 4,896,669 A | 1/1990 | Bhate et al. | |
| 4,946,464 A | 8/1990 | Pevsner | |
| 4,955,899 A | 9/1990 | Del Corna et al. | |
| 5,066,298 A | 11/1991 | Hess | 606/194 |
| 5,071,609 A | 12/1991 | Tu et al. | |
| 5,087,244 A | 2/1992 | Wolinsky et al. | |
| 5,112,304 A | 5/1992 | Barlow et al. | |
| 5,116,318 A | 5/1992 | Hillstead | |
| 5,137,512 A | 8/1992 | Burns et al. | |
| 5,152,782 A | 10/1992 | Kowligi et al. | |
| 5,171,297 A | 12/1992 | Barlow et al. | |
| 5,192,296 A | 3/1993 | Bhate et al. | |
| 5,201,706 A | 4/1993 | Noguchi et al. | |
| 5,211,654 A | 5/1993 | Kaltenbach | |
| 5,213,576 A | 5/1993 | Abiuso et al. | |
| 5,226,880 A | 7/1993 | Martin | |
| 5,236,659 A | 8/1993 | Pinchuk et al. | |
| 5,254,090 A | 10/1993 | Lombardi et al. | |
| 5,256,143 A | 10/1993 | Miller et al. | |
| 5,286,254 A | 2/1994 | Shapland et al. | |
| 5,290,306 A | 3/1994 | Trotta et al. | |
| 5,330,429 A | 7/1994 | Noguchi et al. | |
| 5,338,299 A | 8/1994 | Barlow | |
| 5,342,305 A | 8/1994 | Shonk | |
| 5,348,538 A | 9/1994 | Wang et al. | |
| 5,358,486 A | 10/1994 | Saab | |
| 5,358,516 A | 10/1994 | Myers et al. | |
| 5,366,472 A | 11/1994 | Hillstead | |
| 5,370,618 A | 12/1994 | Leonhardt | |
| 5,403,340 A | 4/1995 | Wang et al. | |
| 5,411,479 A * | 5/1995 | Bodden | 604/101.03 |
| 5,415,636 A | 5/1995 | Forman | |
| 5,425,710 A | 6/1995 | Khair et al. | |
| 5,429,605 A | 7/1995 | Bernd et al. | |
| 5,456,661 A | 10/1995 | Narciso, Jr. | |
| 5,458,568 A | 10/1995 | Racchini et al. | |
| 5,466,252 A | 11/1995 | Soukup et al. | |
| 5,470,313 A | 11/1995 | Crocker et al. | |
| 5,478,320 A | 12/1995 | Trotta | |
| 5,490,839 A | 2/1996 | Wang et al. | |
| 5,496,276 A | 3/1996 | Wang et al. | |
| 5,498,238 A | 3/1996 | Shapland et al. | |
| 5,499,973 A | 3/1996 | Saab | |
| 5,499,980 A | 3/1996 | Euteneuer | |
| 5,499,995 A | 3/1996 | Teristein | |
| 5,500,180 A | 3/1996 | Anderson et al. | |
| 5,500,181 A | 3/1996 | Wang et al. | |
| 5,512,051 A | 4/1996 | Wang et al. | |
| 5,519,172 A | 5/1996 | Spencer et al. | |
| 5,527,282 A | 6/1996 | Segal | |
| 5,529,820 A | 6/1996 | Nomi et al. | |
| 5,609,605 A | 3/1997 | Marshall et al. | |
| 5,613,979 A | 3/1997 | Trotta et al. | |
| 5,620,649 A | 4/1997 | Trotta | |
| 5,641,373 A | 6/1997 | Shannon et al. | |
| 5,718,680 A * | 2/1998 | Kraus et al. | 604/509 |
| 5,728,066 A * | 3/1998 | Daneshvar | 604/96.01 |
| 5,766,201 A * | 6/1998 | Ravenscroft et al. | 606/194 |
| 5,843,116 A * | 12/1998 | Crocker et al. | 606/192 |
| 5,868,704 A | 2/1999 | Campbell et al. | 604/96 |
| 5,919,163 A * | 7/1999 | Glickman | 604/101.05 |
| 6,139,570 A * | 10/2000 | Saadat et al. | 607/105 |
| 6,312,405 B1 * | 11/2001 | Meyer et al. | 604/96.01 |

FOREIGN PATENT DOCUMENTS

| | | |
|---|---|---|
| EP | 0 540 858 | 5/1993 |
| GB | 1566674 | 5/1980 |
| WO | 90/14054 | 11/1990 |
| WO | 94/02185 | 2/1994 |
| WO | 95/05555 | 2/1995 |
| WO | 96/14895 | 5/1996 |
| WO | 97/02791 | 1/1997 |
| WO | 99/02212 | 1/1999 |

* cited by examiner

BALLOON CATHETER AND METHOD OF MOUNTING SAME

BACKGROUND OF THE INVENTION

1. Field of the Invention

The present invention relates to improved balloon catheter devices, and methods of making the same.

2. Description of Related Art

Balloon catheter devices are commonly used for a wide variety of medical procedures today, including temporarily occluding blood or other fluid flow, re-shaping of blood vessels or other body conduits, removing plaque or other obstructions from vessels, and/or delivering or positioning devices within vessels, such as intraluminal stent or stent-graft devices. With on-going advances in minimally invasive medical procedures, such balloon devices continue to grow in popularity and in scope of possible uses.

Traditionally, balloon devices have taken one of two general forms—angioplasty balloons and embolectomy balloons. Angioplasty balloons have generally been constructed from relatively stiff material, such as poly(ethylene terephthalate) (PET), which can be safely inflated to relatively high internal pressures (such as on the order of 10 ATM (1.0 MPa) or more). These balloons generally inflate rapidly to a given maximum diameter and will undergo minimal additional enlargement upon introduction of additional pressure (until they burst under extreme pressures). These balloons are typically used where high pressure is desired, such as to fracture and/or compact hard plaque in a blood vessel or to deliver balloon expandable devices, such as stents. One drawback with stiff angioplasty balloons, however, is that upon deflation they tend to become a crinkled, flattened mass that have dimensions significantly larger than their initial introduction diameter—making them more difficult to remove than to initially introduce. Additionally, these flattened devices in many cases cause adverse interactions between themselves and the devices with which they are conjunctly used.

By contrast, embolectomy balloons are normally constructed from a highly elastomeric material, such as latex, which will enlarge steadily in diameter with a steady increase in internal pressure. These balloons typically are governed by the volume of fluid/liquid used to inflate them rather than an operating pressure, have much lower operating pressures (such as, typically on the order of about 2 ATM (203 kPa) or less) and they tend to continue to grow in diameter upon further introduction of pressure until they ultimately burst. These balloons are typically used in embolic procedures where soft material is repositioned in a vessel. Additionally, the balloon can be formed from a tacky material such as latex that can be used to adhere to soft plaque, thrombus or other undesirable material within a vessel and then withdrawn to remove the undesirable material. Although these balloons have low operating pressures, they do tend to deflate to diameters almost identical to their initial introduction diameters—making them very easy to remove.

It has been a long desired goal to develop a balloon that can withstand the very high pressures required for angioplasty but also has the inflation and deflation characteristics of an embolectomy balloon. The combination of these properties was achieved with the invention of the balloon devices described in U.S. Pat. Nos. 5,752,934 and 5,868,704 to Campbell, et al., and U.S. patent application Ser. No. 08/858,309 to Campbell, et al. These patents describe several important advances in balloon catheter constructions, including how to construct high pressure balloons from expanded polytetrafluoroethylene (PTFE) and an elastomer so as to exhibit steady growth with increasing pressure up to a pre-determined maximum diameter and then readily compact to virtually their initial introduction diameters for easy removal.

The Campbell et al. patents teach how to form a tubular sleeve from expanded PTFE tape and then coat the sleeve with an elastomer. The sleeve is then mounted on a catheter shaft in a manner that allows it to contain expansion liquid (either by mounting the sleeve over an expandable bladder (e.g., a latex or PET balloon) or by rendering the sleeve liquid-tight so as to allow it to serve as the bladder itself). The result is a unique balloon that combines high-pressure performance with compaction to near initial introductory diameter following inflation and deflation. Balloons made in accordance with the Campbell et al. patents have excellent performance characteristics and are particularly suitable for delivery and/or deployment of balloon expandable devices, such as intravascular stents.

Despite the excellent performance characteristics of the Campbell et al. balloons, it is believed that further improvements are desirable in the balloons and their mounting techniques to make them easier to mount on catheter shafts. Further, it is believed that further improvements in balloon performance can be achieved by modifying the mounting techniques, such as to provide a controlled failure mechanism.

SUMMARY OF THE INVENTION

The present invention is an improved method of forming and mounting a distensible balloon catheter, and sleeves used to construct such balloons. One embodiment of the method of the present invention comprises forming a distensible balloon sleeve with non-distensible ends. The sleeve is mounted on the catheter shaft at the non-distensible ends while retaining the distensibility of the balloon as a whole. This construction is easier to mount and more reliable in operation than previous mounting methods. Alternatively or additionally, the balloon may be mounted to the catheter shaft using non-distensible tape that also retains the distensibility of the operative portion of the balloon. The present invention is particularly adapted for use with expanded polytetrafluoroethylene (PTFE) balloons, such as those described in U.S. Pat. Nos. 5,752,934 and 5,868,704 to Campbell, et al.

The mounting techniques of the present invention are further readily adapted to include other beneficial properties, such as inclusion of controlled failure mechanisms. These and other benefits of the present invention will be appreciated from review of the following description.

DESCRIPTION OF THE DRAWINGS

The operation of the present invention should become apparent from the following description when considered in conjunction with the accompanying drawings, in which.

DETAILED DESCRIPTION OF THE INVENTION

The present invention is directed to improved methods of mounting a balloon such as that described in U.S. Pat. Nos. 5,752,934 and 5,868,704 to Campbell, et al. and U.S. patent application Ser. No. 08/858,309 to Campbell et al. (hereafter "Campbell et al. patents"), all incorporated by reference.

The Campbell et al. patents describe improved balloons that combine the ability to safely and predictably achieve high operating pressures with the ability to be introduced at a small initial profile, be fully inflated, and then deflated to nearly the same initial profile for ease of removal. The preferred balloon devices of the Campbell et al. inventions employ multiple wraps using a porous expanded polytetrafluoroethylene (PTFE) tape, such as one made in accordance with U.S. Pat. Nos. 3,953,566 and 4,187,390, incorporated by reference, combined with an elastomeric material, such as a polyurethane, so as to seal the porous structure of the expanded PTFE and render it liquid-tight. The resulting structure can be formed into a tube and then mounted onto a catheter shaft, such as through adhesion using various adhesives and methods. In particular, the mounting methods contemplated by the Campbell et al. patents are described in U.S. Pat. No. 5,752, 934, for example, at: col. 9, lines 25-34; and col. 10, lines 38-44; and in U.S. Pat. No. 5,868,704, for example, at: col. 10, line 60, to col. 11, line 3; col. 12, lines 4-13; and col. 14, line 17, to col. 15, line 8.

Figure 1:
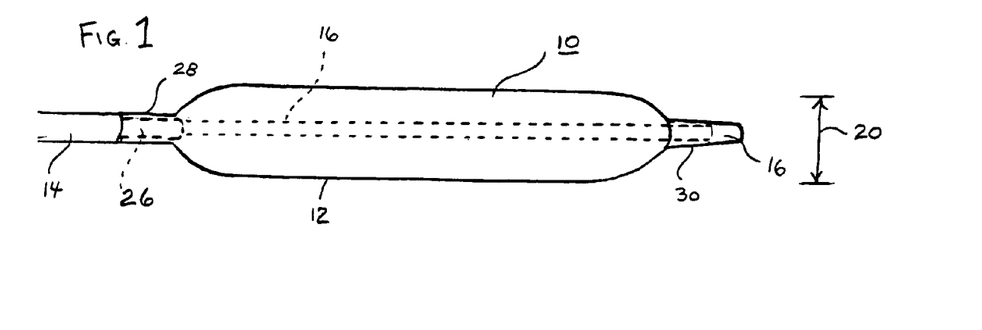
FIG. 1 is a side elevation view of a balloon device made in accordance with the present invention shown, in an inflated orientation.
Figure 2:
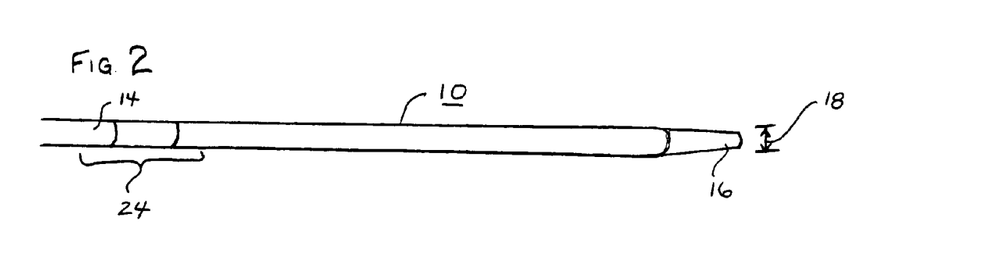
FIG. 2 is a side elevation view of the balloon device of FIG. 1, shown in a deflated orientation.
Figure 3:
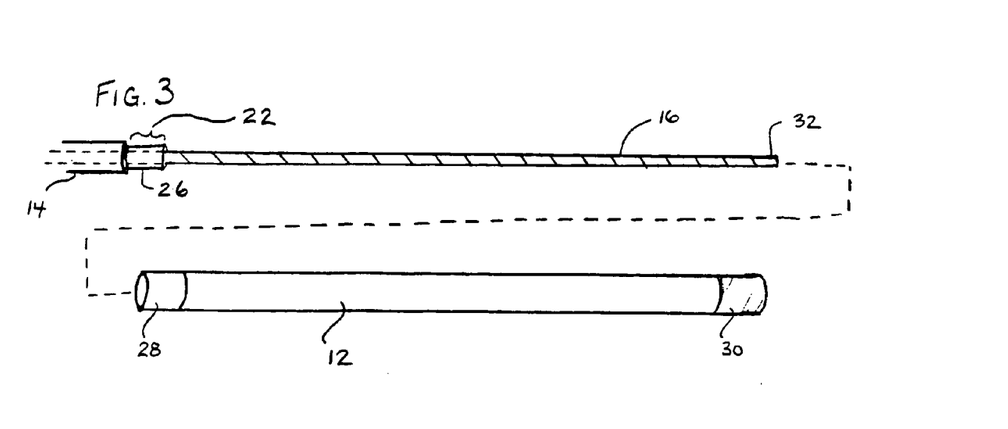
FIG. 3 is an exploded side elevation view of a stepped end of a catheter shaft, an inner member, and a tubular sleeve used to construct a balloon in accordance with the present invention.

While these previous mounting methods function quite well, it has been determined that significant improvements are possible in increasing the speed and ease of mounting of tubular structures onto a catheter shaft in order to form a catheter balloon device. Referring to FIGS. 1 through 3, the present invention comprises an inflatable balloon 10, formed from a tubular sleeve 12 that is mounted onto a catheter shaft 14 and an inner member 16. The balloon 10 is introduced in a compacted, deflated configuration 18, such as that shown in FIG. 2, and then distended to a fully enlarged, inflated configuration 20, such as that shown in FIG. 1.

The catheter shaft 14 preferably has a reduced diameter over a segment 22 adapted to receive the sleeve 12 so that a smooth transition 24 is formed between the catheter shaft 14 and the balloon following mounting, as is shown in FIG. 2. FIG. 3 illustrates a beveled landing 26 that performs this function. By way of example, for a catheter shaft with an outer diameter of about 0.5 to 3.5 mm and a sleeve with a wall thickness of about 0.1 to 0.5 mm, a suitable landing 26 might have a diameter of about 0.5 to 2 mm. The difference in dimensions between the wall thickness and the reduced diameter of the landing can be accounted for by the addition of adhesive and a tape wrap, as is explained below. The length of the landing 26 in this embodiment might range from about 1 to 5 mm.

The sleeve 12 includes a first end 28 and a second end 30. The first end 28 of the sleeve 12 is attached to the landing 26. The second end 30 of the sleeve is attached to the inner member 16 at its distal (that is, "leading") end 32. The sleeve 12 should be constructed from a distensible material, such as an elastomer (e.g., silicone, latex, polyurethane, or from a composite of expanded PTFE and elastomer as described above) that allows the sleeve to be inflated and deflated within normal operating pressures without causing permanent unfolding or deforming of the balloon material. By the term "distensible," it is intended to define a balloon material with a structure that will change in one or more dimensions upon introduction of distention force. Preferably, the balloon material will compact to most or all of its previous dimensions upon removal of the force. In this manner, the balloon will deflate to a "wingless" diameter following inflation, instead of deflating to a flattened, "winged," structure that may be hard to remove, such as that formed by a conventional PET balloon.

It has been determined, however, that distensible material does not always mount successfully to a catheter shaft since the material may tend to separate from the catheter shaft and/or undergo damage during inflation. To address this problem, the present invention treats the ends 28, 30 of the sleeve 12 to render them non-distensible. By the term "non-distensible," it is intended to define a balloon material with a structure that is significantly less compliant under distention force than a distensible main body of the balloon and, preferably, material that will undergo little or no change in dimensions upon introduction of distention force.

As is explained in greater detail below, the ends may be rendered non-distensible through a variety of methods, including by: over-wrapping the ends with non-distensible material, such as a tape; attaching non-distensible structures; coating or permeating the ends with a non-distensible material, such as a fluorinated ethylene propylene (FEP) or cyanoacrylate ester; and/or modifying the structure of the material to render it non-distensible, such as through heat (including laser) treatment. Other possible methods of rendering the ends non-distensible may include insert molding and injection molding.

Once the ends 28, 30 have been rendered non-distensible, the sleeve 12 may be readily mounted on the catheter to form a liquid-tight seal through a number of possible ways, such as through, but not limited to, application or tape, glue, heat bonding, mechanical swaging, or some combination of two or more of these mounting methods. The preferred method of mounting is described below with reference to FIGS. 4 through 6.

Figure 4:
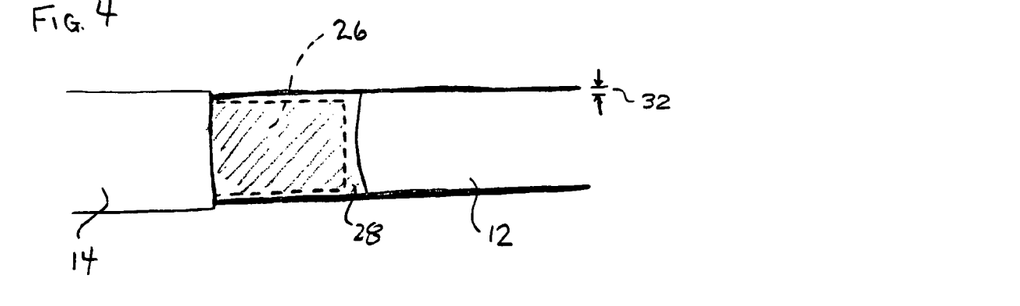
FIG. 4 is an enlarged side elevation view of a sleeve mounted over a stepped end of a catheter shaft.

FIG. 4 illustrates a sleeve 12 positioned over a landing 26 on a catheter shaft 14. The sleeve 12 and landing 26 should be proportioned so that the sleeve fits closely over the landing, with a clearance 32 of about 0.06 mm or less. Preferably, the sleeve 12 fits snugly over the landing 26, with virtually no clearance, so as to resist separation between the sleeve 12 and the catheter shaft 14 upon application of tension on the sleeve 12. An adhesive may be applied to the landing 26 (and/or the interior of the sleeve 12) prior to mounting on the shaft to aid in forming a bond. Suitable adhesives include: UV cure adhesive, cyanoacrylate ester, epoxy, polyurethane, silicone, and melt adhesives such as fluorinated ethylene propylene (FEP). The preferred adhesive is a thin coating of cyanoacrylate ester adhesive applied to the full surface of the landing immediately prior to placing the sleeve 12 on the catheter shaft 14.

Figure 5:
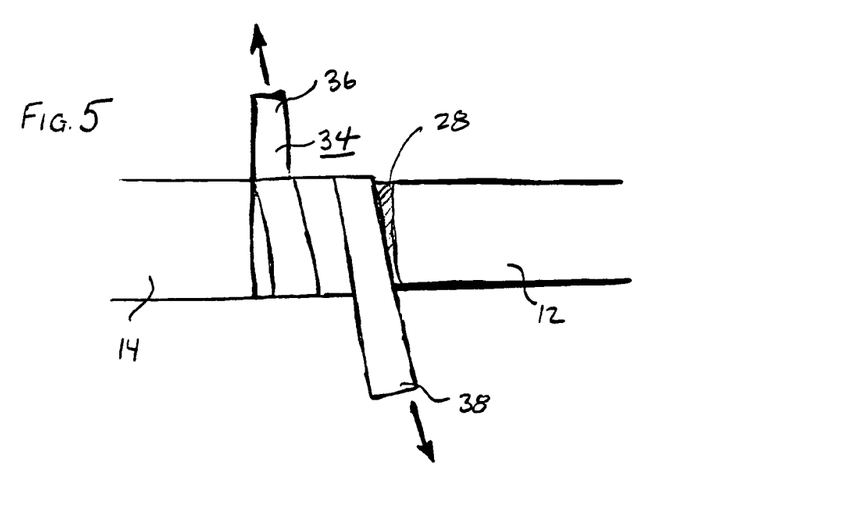
FIG. 5 is the sleeve and stepped end of FIG. 4 with a tape being wrapped around the sleeve to help attach it to the stepped end.
Figure 6:
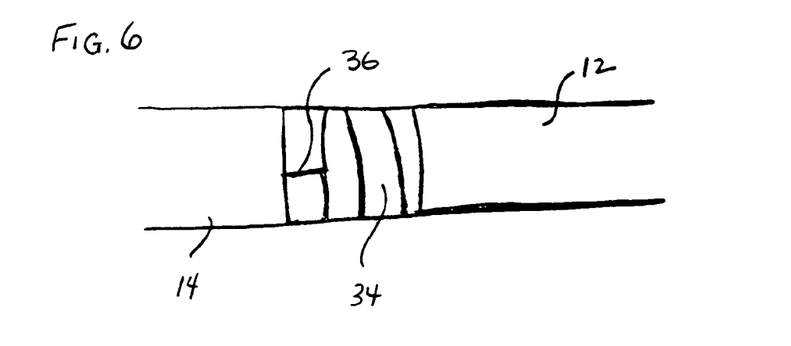
FIG. 6 is the sleeve and stepped end of FIG. 5 with the tape completely mounted over the sleeve on the end of the catheter shaft.

Once the sleeve 12 is positioned on the catheter shaft 14, a tape 34 is wrapped around the end 28, as is shown in FIG. 5. Tension is preferably applied on both ends 36, 38 of the tape as it is wrapped into place. To hold the tape in place, an adhesive should be applied between the wrap layers, such as by applying a drop of cyanoacrylate ester between the layers during the wrapping. Once the tape 34 is completely wrapped around the end 28 to snugly compress the sleeve against the landing, adhesive should be applied to the ends 36, 38 to secure the ends in place, as is shown in FIG. 6.

The tape 34 is preferably formed from a material that is essentially non-distensible in its longitudinal direction. A preferred tape comprises a tape of expanded PTFE having a width of about 1 to 10 mm, a thickness of about 0.01 to 0.02 mm, and a matrix tensile strength in its longitudinal direction of about 50 to 150 kpsi (345 to 1034 MPa) measured using a strain rate of 100% per minute.

A number of alternative mounting techniques can be employed without departing from the present invention. For example, instead of applying a separate adhesive to the tape during the wrapping process, adhesive may be applied to the tape before wrapping and later activated (such as through application of heat, ultra-violet or infared light, solvent activation, pressure activation, etc.). One method is to apply a coating of a thermoplastic polymer, such as polyurethane, to the tape prior to wrapping and then applying heat to the wrapped end to melt the polyurethane coating and bond the wrapping into place. Mounting can also be achieved by directly welding the tape, the sleeve material itself (with or without a tape wrap), and/or the catheter material into a sealed bond between the catheter and the sleeve, whether by application of heat, solvent, or other means.

The choice of materials should be selected so that bonding may be achieved without adversely affecting component performance. For example, if a catheter shaft of PEBA is employed with a composite balloon of expanded PTFE and polyurethane, the bonding melt temperature should be about 160° and maintained below 180° C.

Other alternative mounting techniques may include: compression fitting ("swaging"); solvent welding, ultrasonic welding; laser welding; radio frequency ("rr") welding; etc.

Figure 7:
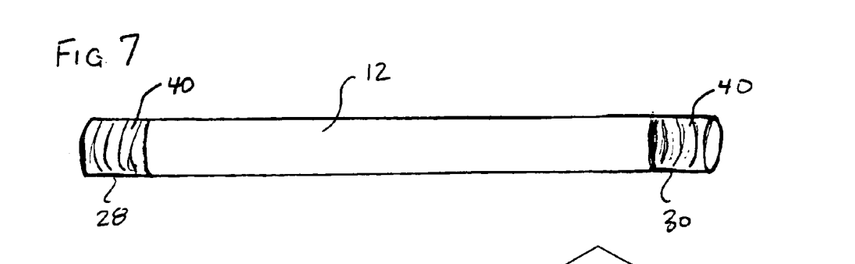
FIG. 7 is a three-quarter elevation view of a further improved sleeve for use with the present invention.

As has been noted, the ends 28, 30 of the sleeve 12 are preferably rendered non-distensible prior to mounting. To accomplish this, a number of techniques can be applied. FIG. 7 illustrates a sleeve 12 that has had a non-distensible tape 40 applied around its ends 28, 30. One effective technique is to place the sleeve on a mandrel and then apply the tape in the manner previously described with respect to the sealing technique described above with respect to FIGS. 4 through 6. The mandrel may then be removed once the ends have been properly treated.

Figure 8:
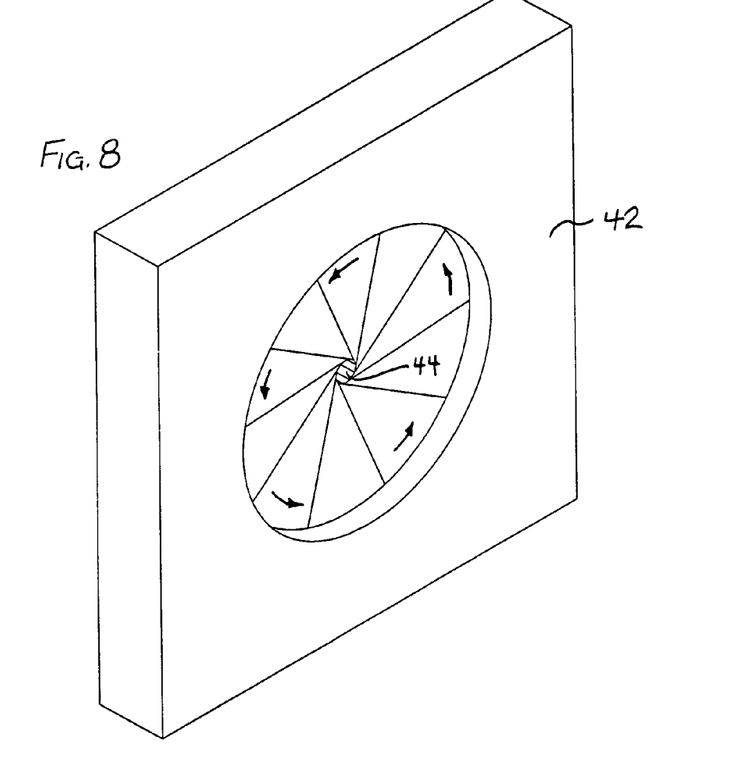
FIG. 8 is a three-quarter elevation view of an apparatus suitable for forming the sleeve of FIG. 7.

Another technique is to heat treat the ends 28, 30 to reduce the material's distensiblity and profile in the end regions. One preferred method is to employ an oven 42 with a contractible iris 44 as is shown in FIG. 8. To treat a sleeve 12 of expanded PTFE and elastomer, as previously described, the oven 42 should be set to about 70 to 165° C. Again, the sleeve 12 should be temporarily mounted on a mandrel to hold it in a proper orientation during the heat-treating process. The iris 44 is closed around the sleeve and compressed under a compressive force for about 1 to 30 seconds.

Alternative methods for rendering the ends of the sleeve 12 non-distensible include addition of metal bands, shrink tubing, plastic bands, wire wrap, use of non-distensible materials at the ends of the balloon, etc. Profile reduction may also be achieved through internal material removal, such as through grinding, solvent, or laser removal, or through material thickness reduction at the ends by thinning through relative elongation (e.g., stretching) of the ends. Additionally, distensible material may be removed from the ends, with other, non-distensible, materials possibly being substituted in that area.

Formed in this manner, a balloon made in accordance with the present invention retains all of the properties previously described with respect to the previous Campbell et al. balloons, while being faster, easier, and more reliable to mount on a catheter shaft.

The present invention may be further refined to provide other beneficial properties. For example, the mounting technique may be modified to provide for controlled failure if the balloon is ever accidentally over-inflated to a bursting pressure. One concern with any balloon material is that if the balloon is over-pressurized and bursts in a patient's body, small fragments of the burst balloon may be difficult or impossible to recover—potentially leading to very serious health problems for the patient. In this respect, it would be desirable to provide a mechanism for a balloon to fail in a completely controlled manner if over-inflation ever occurs so that all fragments of the balloon remain together following rupture or to ensure failure of another sub-system of the device prior to rupture of the actual balloon material.

Figure 9:
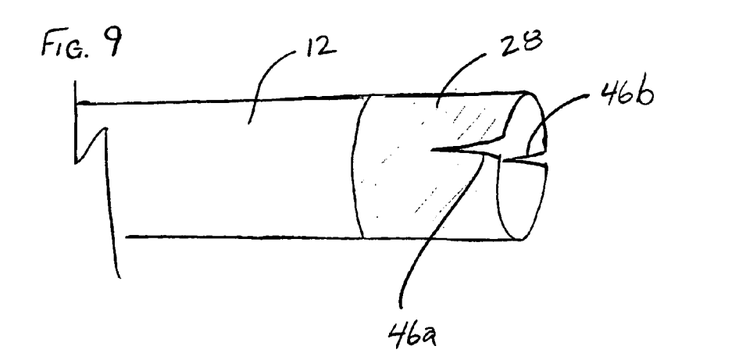
FIG. 9 is an enlarged three-quarter elevation view of a modified end of a sleeve for use with the present invention, the sleeve being provided with slits for providing controlled failure ruptures with the present invention.
Figure 11:
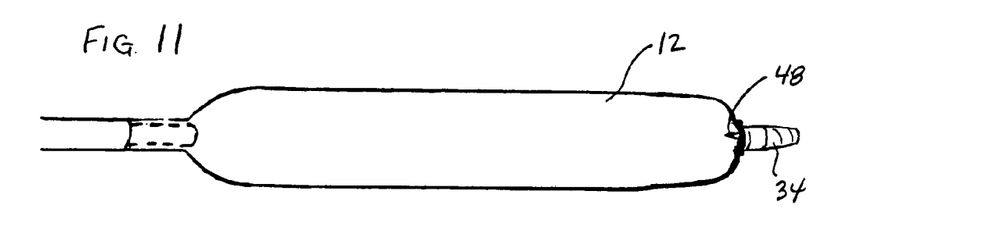
FIG. 11 is a side elevation view of the balloon device of FIG. 10 with the balloon over-inflated, which partially dislodges its mounting tape so as to uncover and begin to active the means to provide controlled failure ruptures.
Figure 12:
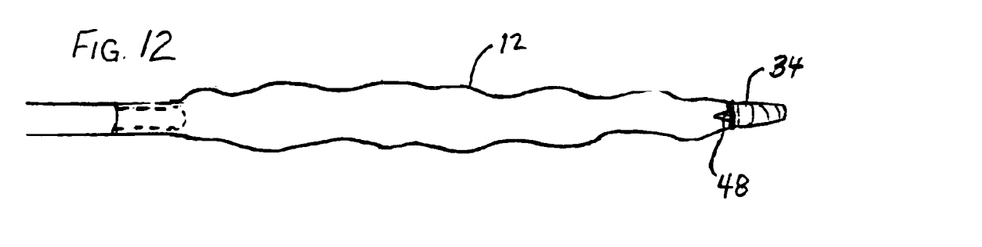
FIG. 12 is a side elevation view of the balloon device of FIG. 11, showing the balloon deflating as a result of the controlled failure mechanism.

One such method of accomplishing controlled failure is to form one or more apertures through the sleeve 12 that will release pressure prior to the balloon bursting—causing a predictable and controlled pressure release that does not result in fragment formation. FIG. 9 illustrates one such method of treating the sleeve 12 by forming one or more slits 46a, 46b in at least one of the ends 28 (and/or 30) that will be sealed under mounting tape 34 prior to failure but will uncover once the balloon becomes over-expanded. The slits may be formed at any point during construction, but are most easily applied after the ends have been rendered non-distensible. This process of progressively exposing the slit is shown in FIGS. 10 through 12.

Figure 10:
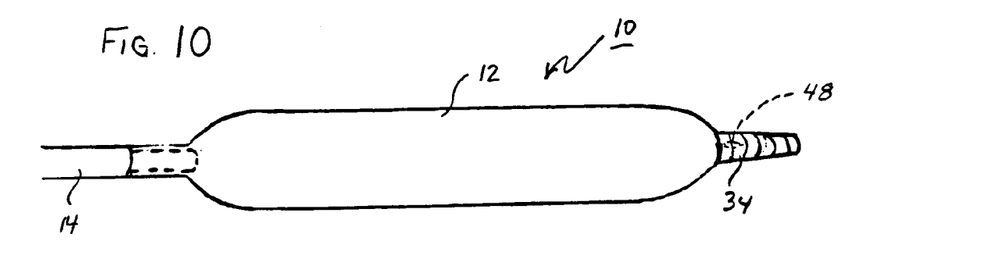
FIG. 10 is a side elevation view of a balloon device made in accordance with the present invention incorporating another embodiment of means to provide controlled failure with the present invention.

Shown in FIG. 10 is another embodiment of a weakened section, in this instance a small oval hole 48 formed in end 30. During normal operation, the hole 48 is completely concealed under the mounting tape 34. However, if the balloon 10 is ever over-inflated, as is shown in FIG. 11, the tape 34 will fold toward distal end 52, progressively uncovering hole 48. Once the hole 48 is uncovered, the inflation liquid, causing excessive pressure in the balloon, will begin leaking through the hole 48. In this manner the balloon can be prevented from exploding and fragmenting—allowing the failed balloon to be removed in one piece.

Other methods of providing controlled failure of the balloon include: weakening the wall (without fully penetrating it) through use of a cut through only part of the sleeve wall; weakening the wall in a predetermined location by altering its structure through use of a laser, heat, mechanical means, or chemical reaction; reinforcing the sleeve in all but certain segments that are intended to fail (such as through a coating process); controllably degrading the elastomeric component so that failure constitutes leaking through the balloon material rather than rupture; selecting an elastomer that fails at a desired failure diameter; etc.

Without intending to limit the present invention to the specifics described hereinafter, the following examples illustrate how the present invention may be made.

Example 1

A 7.62 mm wide length of porous expanded PTFE film is wrapped onto a 4.0 mm diameter metal mandrel at a pitch of about 2.54 mm per mandrel revolution so that about 3 overlapping layers cover the mandrel. Following this wrap, another 3 layers of the same film are applied over the first 3 overlapping layers, using the same pitch but in the opposite direction. This method of single-pass application is repeated a total of six times, so that finally, a total of 18 helical overlapping layers are applied onto the mandrel.

With the wrapping complete, the mandrel and overlying expanded PTFE film are placed in an air convection oven set at about 380° C. for about 18 minutes to heat-bond the adjacent layers of film, then removed and allowed to cool. The resulting 4.0 mm inner diameter film tube formed from the helically wrapped layers of film is then removed from the mandrel.

The film tube is then tensioned longitudinally, simultaneously reducing in diameter and lengthening until it reaches approximately 4.5 times its length while on the 4.0 mm mandrel post heat-bonding. The tube is then coaxially fitted over a 3.8 mm diameter metal mandrel. This coaxial fitting is done carefully, ensuring that the diameter increase experienced by the film tube occurs in a consistent manner, and that the tube is not damaged. With the coaxial fitting complete, the film tube is measured to be approximately twice its length while on the 4.0 mm mandrel post heat-bonding. The film tube is then carefully removed from the 3.8 mm mandrel.

Removed from the 3.8 mm mandrel, a knot is created at one end of the film tube while a 3.0 mm metal tube is inserted coaxially into the other end of the film tube. The metal tube and the overlying film tube are then submerged into a 4% (4 g per 100 ml) solution of TT-1070A TECOTHANE® resin manufactured by Thermedics Inc. (Woburn, Mass.) in tetrahydrofuran manufactured by J. T. Baker (Phillipsburg, N.J.). The metal tube and the overlying film tube are situated such that the knotted end of the film tube is submerged completely, but the open end of the film tube and the open end of the metal tube are not. In this manner, the TECOTHANE® solution is in direct contact with the outside of the film tube for approximately one minute. The metal tube and the film tube are then removed from the TECOTHANE® solution, and the film tube (still wet with solution) is then carefully removed from the metal tube and allowed to dry at ambient temperature for approximately 30 minutes. Care is taken to avoid any folding of the film tube.

Next, the film tube is placed within an INSTRON® tensile test machine equipped with flat-faced jaws, and tensioned longitudinally at a rate of 200 mm/min until a load of 9.5 kg is achieved. Once this tension is achieved, the film tube is held at fixed length and subjected to heat from a hot air gun until the load indicator on the INSTRON® tensile testing machine reads 2.3 kg. The heat is such that it accelerates the force declination, but does not affect the TECOTHANE® material adversely. The upper jaw of the testing machine is then opened, and a 0.43 mm stainless steel wire is fitted coaxially within the longitudinally pulled film tube. The upper jaw is positioned such that it fully engages the film tube, but not the resident wire, and closed. The film tube is then subjected to heat from the hot air gun and tensioned longitudinally again, at a rate of 200 mm/min, until a load of 8.7 kg is achieved. Once this tension is achieved, the film tube is again held at fixed length, with continued heat from the hot air gun, until the load indicator on the INSTRON® tensile testing machine reads 3.5 kg. The ends of the film tube are then secured to the wire to prevent longitudinal shrinkage, and the film tube and wire assembly are removed from the tensile test machine.

Additional expanded PTFE film is then helically applied to the outer surface of the film tube to inhibit wrinkling in the subsequent step. The securing means between the film tube and the underlying wire are removed. The tube is then compressed longitudinally, reducing the tube length to approximately 0.6 of the length just prior to this compression step. Care is taken to ensure a high degree of uniformity of compression along the length of the tube. The additional outer film is then removed from the longitudinally compressed film tube, and the film tube is cut at each end to expose approximately 2.0 cm of the wire underneath.

A blunt tipped needle with a female luer connector at one end, approximately 36 mm long, having 1.27 mm outer and 0.84 mm inner diameter, is inserted coaxially between the film tube and the 0.43 mm wire. A vacuum pump is then connected, by means of a male luer, to the female luer equipped needle at the end of the film tube, and the lumen of the film tube, via the needle, is subjected to negative pressure. The entire assembly consisting of the wire, film tube, and needle is then attached to a variable speed linear slide.

The slide is used to dip the assembly, with the vacuum pump running into a 10% (10 g per 100 ml) solution of TT-1070A TECOTHANE® resin manufactured by Thermedics Inc. (Woburn, Mass.) in tetrahydrofuran manufactured by J. T. Baker (Phillipsburg, N.J.). The assembly is dipped to the point where about 5 mm of the film tube, covering the blunt needle, is within the solution. The assembly remains within the solution for approximately 30 seconds, after which the linear slide, set at a speed of 3.7 mm/sec is used to remove the assembly. The 3.7 mm/sec speed is chosen because it yields a continuous, uniform coating of solution on the surface of the film tube. Once completely removed from the solution, the assembly is disconnected from the linear slide and the vacuum pump, and allowed to dry at ambient temperature for approximately 30 minutes. Care is taken to keep the assembly oriented in a vertical position to maintain the uniformity of the TECOTHANE® coating.

With the solution dry, the film tube is left with a thin coating of TT-1070A TECOTHANE® material on its outer surface. The portion of the film tube covering the blunt needle (along with the needle itself) is removed from the rest of the film tube. Likewise, a portion approximately 1.0 cm long is removed from the other end of the film tube. The remaining film tube portion is then carefully removed from the coaxially fitted 0.43 mm wire. Next, a small bevel cut is made at one end of the film tube. A 0.71 mm wire is used to push the point of the beveled end within the lumen of the coated film tube. The same wire is then carefully used to continue pushing the beveled end further and further within the lumen of the film tube, until finally, the beveled end passes completely through the length of the tube. The coating, which originally was on the outer surface of the tube, is now on the inner surface. This is done very carefully, so that no substantial lengthening of the tube occurs.

A portion of this balloon material is fitted coaxially onto a stepped steel mandrel which is wrapped manually with thin expanded PTFE film. Prior to being wrapped with film, the outer diameter of the large end of the mandrel is about 0.97 mm, and the outer diameter of the small end is about 0.71 mm. Once the mandrel is wrapped, the outer diameter of the large end of the mandrel is about 1.02 mm, and the outer diameter of the small end is about 0.74 mm. Isopropyl alcohol is used as a lubricant to ease the mounting of the balloon portion such that approximately 3.5 mm of material covers the large section of the stepped mandrel. The stepped mandrel, with the overlying balloon portion, is then placed into an air convection oven set at 80° C. for approximately 5 minutes in order to evaporate the isopropyl alcohol. Upon removal from the oven, the outer diameter of the large (proximal) end of the balloon portion is about 1.37 mm, and the outer diameter of the small (distal) end is about is 1.14 mm.

In an effort to reduce the outer diameters at both ends of the balloon material, a 3.5 mm section at each end of the balloon is treated within a heated contractible iris. The heated iris comprises of 15 metal wedges having a depth about of 6 mm, rotationally driven by a 20.0 mm diameter air piston with an input air pressure of about 241 kPa. The iris is adjusted to a temperature of 80° C., and a final contracted diameter of approximately 1.04 mm. A length of silicone tubing having an inner diameter of about 1.39 mm and an outer diameter of about 1.68 mm is fitted coaxially over the balloon material, and each end of the balloon (underneath the silicone tubing) is compressed for a 1 second cycle, and then a 7 second cycle. Following compression, the outer diameter of the proximal end of the balloon portion is 1.22 mm, and the outer diameter of the distal end is about 1.02 mm.

Next, small diameter reinforcing tubes are fabricated for the purpose of rendering the compressed ends of the balloon portion non-distensible. Since each end of the balloon portion is of different outer diameters, two reinforcing tubes are created. The reinforcing tube corresponding to the proximal end of the balloon portion is fabricated by helically wrapping 19.06 mm wide expanded PTFE film about a 1.24 mm diameter mandrel at a pitch of about 2.54 mm per mandrel revolution so that 7 to 8 overlapping layers covers the mandrel. Following these wraps, another 7 to 8 layers of the same film are applied over the first 7 to 8 overlapping layers, using the same pitch but in the opposite direction. This method of application is repeated a total of six times, so that finally, a total of 42 to 48 helical overlapping layers are applied onto the mandrel. With the wrapping complete, the mandrel and overlying expanded PTFE film are placed in an air convection oven set at 370° C. for about 8 minutes. The reinforcing tube corresponding to the distal end of the balloon portion is fabricated in the same manner as that of the proximal reinforcing tube, but employs a 1.02 mm mandrel.

With the reinforcing tubes complete, a 3.0 mm long section is cut from each, forming two collars. Next, the outer surface of each compressed end of the balloon portion is treated with 7701 MEDICAL GRADE PRIMER manufactured by Loctite Corporation (Hartford, Conn.), and allowed to dry for approximately 15 minutes. A thin coating of 4981 INSTANT MEDICAL DEVICE ADHESIVE manufactured by Loctite Corporation (Hartford, Conn.), is then applied to the outer surface of the proximal end of the balloon portion, and the 3.0 mm long section of proximal reinforcing tube is fitted coaxially over the coated end. Any surplus adhesive is quickly wiped off, and digital pressure is applied to the reinforcing tube and the underlying balloon for approximately 1 minute. At this point, the outer diameter of the proximal end is about 1.47 mm. In an effort to reduce the outer diameter of the now reinforced proximal balloon end, the 3.5 mm long end region is covered by silicone tubing, inserted into the heated iris as previously described, and compressed for a 1 second cycle, twice. The balloon end is then repositioned within the iris such that the outer most edge of the proximal end resided approximately 3 mm within the 6 mm deep iris, and compressed again for a 7 second cycle. These compression cycles result in a final proximal end diameter of about 1.37 mm. The procedure for adhesive application, fitting of the reinforcing tube and diameter compression is repeated for the distal end of the balloon. The diameter of the distal end after placement of the reinforcing tube is about 1.24 mm. The diameter of the distal end post compression is about 1.17 mm.

The balloon portion, with reinforced non-distensible ends is now finished and ready to be mounted onto a shaft assembly. To do so, the balloon portion is carefully removed from the underlying mandrel. The balloon portion and the mandrel are dowsed with isopropyl alcohol, and the balloon portion is carefully slid off the mandrel in the distal direction. Once off the mandrel, the balloon portion is inspected for damage. Any remnants of the film used to wrap the mandrel are removed from the interior of the portion, and any residual alcohol on the portion is allowed to evaporate.

A segment of extruded polyethylene tubing of about 0.71 mm inner diameter and about 0.94 mm outer diameter and approximately 29.0 cm in length is fitted coaxially onto a 0.69 mm diameter mandrel of slightly longer length such that the mandrel protrudes from each end of the tubing. A 3.5 mm length of one of the tubing ends is treated with 7701 MEDICAL GRADE PRIMER, and allowed to dry for approximately 15 minutes. A thin coating of 4981 INSTANT MEDICAL DEVICE ADHESIVE is then carefully applied to the same end, and the proximal end of the balloon portion is then fitted coaxially over the 0.69 mm mandrel and onto this region. Any surplus adhesive is quickly wiped off, and digital pressure is applied to the balloon end and the underlying tubing for approximately 1 minute. Great care is taken to ensure that no adhesive was applied to the 0.69 mm diameter mandrel. The outer diameter of the balloon end at this point is 1.42 mm. To reduce the outer diameter of the proximal balloon end now attached to the tubing, the 3.5 mm long end region is covered by silicone tubing, inserted into the heated iris as previously described, and compressed for a 1 second cycle, twice. The balloon end is then repositioned within the iris such that the outer most edge of the proximal end resided approximately 3 mm within the 6 mm deep iris, and compressed again for a 7 second cycle. These compression cycles result in a final proximal end diameter of 1.27 mm. The 0.69 mm mandrel is then carefully removed from the tubing.

Next, a segment of extruded polyethylene tubing of 0.46 mm inner diameter and 0.58 mm outer diameter approximately 38 cm in length is fitted coaxially onto a 0.41 mm diameter mandrel of slightly longer length such that the mandrel protruded from each end of the tubing. The tubing, and the resident mandrel are then fitted coaxially within the lumen of the tubing to which the balloon is attached. This is achieved by sliding the smaller tubing and resident mandrel into the lumen of the larger tubing at its bare end, using isopropyl alcohol as a lubricant to aid the passing of the smaller tubing through the attached balloon. Care is taken to avoid damaging or significantly lengthening the attached balloon, and to ensure that the smaller tubing extended approximately 3 cm beyond the distal end of the balloon. The alcohol is allowed to evaporate, then a 3.5 mm length region of the smaller tubing extending beyond the distal end of the balloon is treated with 7701 MEDICAL GRADE PRIMER, and allowed to dry for approximately 15 minutes. A thin coating of 4981 INSTANT MEDICAL DEVICE ADHESIVE is then carefully applied to this region, and the balloon and attached tubing are then slid such that the 3.5 mm distal balloon end covered this region. Any surplus adhesive is quickly wiped off, and digital pressure is applied to the balloon end and the underlying tubing for approximately 1 minute. The outer diameter of the distal balloon end at this point is 1.19 mm. To reduce the outer diameter of the distal balloon end now attached to the inner tubing, the 3.5 mm long end region is covered by silicone tubing, inserted into the heated iris as previously described, and compressed for a 1 second cycle, twice. The balloon end is then repositioned within the iris such that the outer most edge of the distal end resides approximately 3.0 mm within the 6 mm deep iris, and is compressed again for a 7 second cycle. These compressions result in a final distal end diameter of 1.12 mm.

The balloon portion, successfully attached to the tubing in a coaxial configuration, defines a finished prototype balloon catheter, which is ready to be inflated. To affect a suitable inflation, a female luer fitting in a "Y" configuration is fitted with hydrostatic adapters at two of its three openings. This assembly is placed over the bare ends of the tubing such that one hydrostatic adapter is situated on the small diameter tubing, and the other on the large diameter tubing. This placement leaves one of the openings of the "Y" fitting able to interface with a hand held inflation device commonly used to inflate balloon catheters, and allowed communication of inflation liquid between the inflation device and the annular space between the coaxially arranged large and small diameter tubing. The prototype balloon is inflated at room temperature steadily to approximately 1.6 MPa, and maintained at 1.6 MPa for approximately 1 minute. The balloon inflated consistently, exhibiting a relatively uniform outer diameter, with no leakage at either of the two ends at which the balloon is attached to the underlying tubing. The balloon is then deflated, and subsequently reinflated steadily until failure occurs due to leakage at the attachment sites. The failure occurs at approximately 3.0 MPa.

Example 2

In an alternative embodiment, a portion of balloon material described in Example 1 is fitted coaxially onto a steel mandrel having an outer diameter of 0.71 mm. Isopropyl alcohol is used as a lubricant to ease the mounting of the balloon portion. The mandrel, with the overlying balloon portion, is then placed into an air convection oven set at 80° C. for approximately 5 minutes in order to evaporate the isopropyl alcohol. Upon removal from the oven, the outer diameters of each end of the balloon portion are 1.00 and 1.10 mm.

To reduce the outer diameters at the ends of the balloon material, a 3.5 mm section at each end of the balloon is treated within a heated contractible iris as described in Example 1, using the same settings with exception of the air input pressure, which is adjusted to 103 kPa. As in the case of Example 1, a length of silicone tubing having an inner diameter of 1.39 mm, and an outer diameter of 1.68 mm is fitted coaxially over the balloon material. Each end of the balloon (underneath the silicone tubing) is then compressed for a 7 second cycle. Following compression, the outer diameters of the each end of the balloon portion are 0.95 and 1.01 mm.

Next, a small diameter reinforcing tube is fabricated for the purpose of dimensionally stabilizing the compressed ends of the balloon portion. The reinforcing tube is fabricated by helically wrapping 6.36 mm wide expanded PTFE film about a 1.04 mm diameter mandrel. The film is tensioned such that it necked to a width of approximately 3.84 mm, and is applied at a pitch of 1.28 mm per mandrel revolution so that approximately 3 overlapping layers cover the mandrel. Following this, another 3 layers of the same film are applied over the first 3 overlapping layers using the same pitch, but in the opposite direction, so that a total of approximately 6 helical overlapping layers are applied onto the mandrel. With the wrapping complete, the mandrel and overlying expanded PTFE film are placed in an air convection oven set at 380° C. for 7 minutes, cooled, and cut into 3.0 mm sections to form collars.

Each compressed end of the balloon portion is treated with 7701 MEDICAL GRADE PRIMER manufactured by Loctite Corporation (Hartford, Conn.), and allowed to dry for approximately 15 minutes. A thin coating of 4981 INSTANT MEDICAL DEVICE ADHESIVE, also manufactured by Loctite Corporation, is then applied to the outer surface of each end of the balloon portion, and 3.0 mm long sections of reinforcing tube are fitted coaxially over the each coated end. Any surplus adhesive is quickly wiped off, and digital pressure is applied to the sections of reinforcing tube and the underlying balloon for approximately 1 minute. At this point, the outer diameters of the ends are 1.08 and 1.07 mm. In an effort to reduce the outer diameters of the now reinforced balloon ends, the 3.5 mm long end regions are covered by silicone tubing, inserted into the heated iris as previously described, and compressed for a 2 second cycle, then rotated approximately 90°, and compressed for another 2 second cycle. These compression cycles result in final end diameters of 1.07 and 0.99 mm.

A 1.07 mm diameter stainless steel wire is heated using a model 210-A hot air station manufactured by Beahm (Los Gatos, Calif.) set at 400° C. The heated wire is used to flare a 3.5 mm section of one end of extruded polyethylene tubing having a 0.76 mm inner and 1.04 mm outer diameter, approximately 21.0 cm in length. A thin coating of 4981 INSTANT MEDICAL DEVICE ADHESIVE was then carefully applied to the outer surface of one reinforced end of the balloon portion, and the flared end of the polyethylene tubing is then fitted coaxially over the 0.71 mm mandrel and onto this reinforced end. Any surplus adhesive is quickly wiped off, and digital pressure is applied to the tubing and the underlying balloon for approximately 1 minute. Great care is taken to ensure that no adhesive is applied to the 0.71 mm diameter mandrel. The outer diameter of the flared tubing end at this point is 1.22 mm. In an effort to reduce the outer diameter of the tubing end now attached to the balloon, the 3.5 mm long end region is covered by silicone tubing, inserted into the heated iris, as previously described, and compressed for a 1 second cycle, then rotated approximately 90°, and compressed for another 1 second cycle. These compression cycles result in a final tubing end diameter of 1.21 mm. The portion, the tubing, and the 0.71 mm mandrel are then dowsed with isopropyl alcohol, and carefully slid off the mandrel. Once off the mandrel, the portion and the tubing are inspected for damage, and any residual alcohol is allowed to evaporate. At this point, the balloon portion with non-distensible ends is ready to be mounted onto a shaft assembly.

Next, a segment of extruded polyethylene tubing of 0.46 mm inner diameter and 0.58 mm outer diameter approximately 38.0 cm in length was fitted coaxially onto a 0.41 mm diameter mandrel of slightly longer length such that the mandrel protrudes from each end of the tubing. The tubing and the resident mandrel are then fitted coaxially within the lumen of the tubing to which the balloon is attached. This is achieved by sliding the smaller tubing and resident mandrel into the lumen of the larger tubing at its bare end, using isopropyl alcohol as a lubricant to aid the passing of the smaller tubing through the attached balloon. Care is taken to avoid damaging the attached balloon, and to ensure that the smaller tubing extends approximately 1.5 cm beyond the free end of the balloon. The alcohol is allowed to evaporate, then a 3.5 mm length region of the smaller tubing extending beyond the free end of the balloon is treated with 7701 MEDICAL GRADE PRIMER, and allowed to dry for approximately 15 minutes. A thin coating of 4981 INSTANT MEDICAL DEVICE ADHESIVE is then carefully applied to this region, and the balloon and attached tubing are then slid such that the 3.5 mm balloon end covered this region. Any surplus adhesive is quickly wiped off, and digital pressure is applied to the balloon end and the underlying tubing for approximately 1 minute. The outer diameter of the balloon end at this point is 1.11 mm. To reduce the outer diameter of the balloon end now attached to the inner tubing, the 3.5 mm long end region is covered by silicone tubing, inserted into the heated iris, as previously described, and compressed for a 1 second cycle, three times, rotating the region approximately 60° between each. These compression cycles result in an end diameter of 0.93 mm.

A 0.97 mm diameter stainless steel wire is heated using a model 210-A hot air station manufactured by Beahm set at 400° C. The heated wire is used to flare a 3.5 mm section of one end of extruded polyethylene tubing having a 0.76 mm inner and a 1.04 mm outer diameter, approximately 1.0 cm in length. A thin coating of 4981 INSTANT MEDICAL DEVICE ADHESIVE is then carefully applied to the reinforced end of the balloon portion attached to the smaller diameter tubing. The flared end of the polyethylene tubing is then fitted coaxially over the 0.41 mm diameter mandrel, the smaller tubing, and onto this reinforced end. Any surplus adhesive is quickly wiped off, and digital pressure is applied to the tubing and the underlying balloon for approximately 1 minute. Great care is taken to ensure that no adhesive is applied to the 0.41 mm diameter mandrel. The outer diameter of the flared tubing end at this point is 1.14 mm. In an effort to reduce the outer diameter of the tubing end now attached to the balloon, the 3.5 mm long end region is covered by silicone tubing, inserted into the heated iris as previously described, and compressed for a 1 second cycle, three times, rotating the region approximately 60° between each. These compression cycles result in a final tubing end diameter of 1.11 mm.

Figure 13:
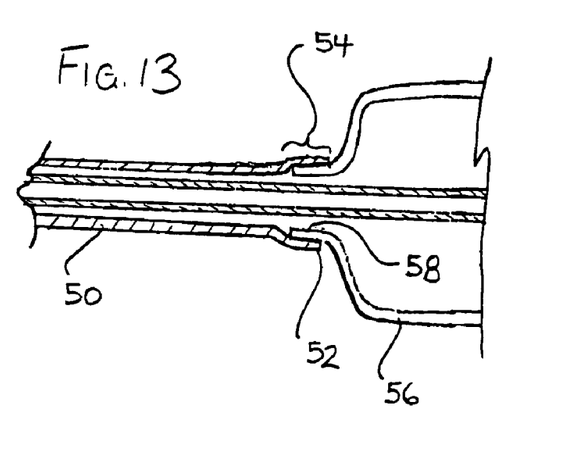
FIG. 13 is a partial longitudinal cross-section view of another embodiment of a balloon device of the present invention.

Unlike the embodiment illustrated in FIGS. 1 through 4, above, this embodiment of the present invention results in the balloon material being mounted inside the catheter shaft. This structure is illustrated in FIG. 13. The catheter shaft 50 is flared at its end 52 and forms a collar 54 around balloon material 56. This unique construction further limits distention of end 58 of the balloon material 56 and forms a tight interference fit between the collar and the balloon under pressure.

The balloon material, successfully attached to the tubing in a coaxial configuration, defines a finished prototype balloon catheter, which is ready to be inflated. To affect a suitable inflation, a female luer fitting in a "Y" configuration is fitted with hydrostatic adapters at two of its three openings. This assembly is placed over the bare ends of the tubing such that one hydrostatic adapter is situated on the small diameter tubing, and the other on the large diameter tubing. This placement leaves one of the openings of the "Y" fitting able to interface with a hand held inflation device commonly used to inflate balloon catheters, and allows communication of inflation liquid between the inflation device and the annular space between the coaxially arranged large and small diameter tubing. The prototype balloon is inflated at room temperature steadily until failure occurs due to leakage at the attachment sites. The failure occurs at approximately 1.4 MPa.

Example 3

Figure 14:
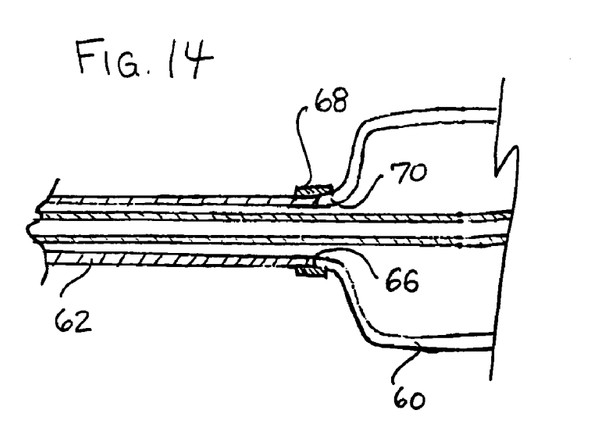
FIG. 14 is a partial longitudinal cross-section view of yet another embodiment of a balloon device of the present invention.

Still another example of attachment of a sleeve 60 of the present invention to a catheter shaft 62 is illustrated in FIG. 14. In this Example, the sleeve 60 is mounted to the catheter shaft 64 as an end-to-end butt joint 66, similar to that previously described with respect to FIGS. 1 through 4 except that no landing is employed. The butt-joint 66 is believed to be easier to construct and employ for some applications. The butt-joint 66 may be held together with a tape wrap, as previously described, or through use of a collar 68, formed from a shrink tube plastic or similar material. Again, the collar 68 is preferably formed from an essentially non-distensible material to further limit distention of the sleeve 60 end 70 when the balloon is inflated.

It should be understood that the present invention may be modified and further refined without departing from its intended scope. In particular, materials and construction specifications may be readily changed to address specific application needs. For example, although the above description and examples are directed to coaxial catheter shafts, the present invention may also be applied to multi-lumen catheter shafts.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A sleeve adapted to be mounted on a catheter shaft so as to be formed into an inflatable balloon comprising
the sleeve having a first end, a second end, and a middle section;
wherein prior to being formed into the balloon by mounting on the catheter shaft at least one of the ends is non-distensible while the middle section of the sleeve is distensible.

2. The sleeve of claim 1 wherein the sleeve is mounted on a catheter shaft to form an inflatable balloon.

3. The sleeve of claim 2 wherein the sleeve forms a liquid-tight seal at the ends to the catheter shaft.

4. The sleeve of claim 1 wherein the at least one end is tape wrapped to render it non-distensible.

5. The sleeve of claim 1 wherein the at least one end has a coating to render it non-distensible.

6. The sleeve of claim 1 wherein the at least one end has a modified structure that renders it non-distensible.

7. The sleeve of claim 1 wherein the at least one end is covered with an essentially non-distensible material to render it non-distensible.

8. The sleeve of claim 7 wherein the essentially non-distensible material comprises a reinforcing collar.

9. The sleeve of claim 1 wherein the at least one end is attached with adhesive to a non-distensible material to render it non-distensible.

10. The sleeve of claim 1 wherein the sleeve comprises a fluoropolymer.

11. The sleeve of claim 10 wherein the fluoropolymer comprises a polytetrafluoroethylene.

12. The sleeve of claim 2 wherein the at least one end is tape wrapped to render it non-distensible.

13. The sleeve of claim 2 wherein the at least one end has a coating to render it non-distensible.

14. The sleeve of claim 2 wherein the at least one end has a modified structure that renders it non-distensible.

15. The sleeve of claim 2 wherein the at least one end is covered with an essentially non-distensible material to render it non-distensible.

16. The sleeve of claim 15 wherein the essentially non-distensible material comprises a reinforcing collar.

17. The sleeve of claim 2 wherein the at least one end is attached to a non-distensible material to render it non-distensible.

18. The sleeve of claim 2 wherein the sleeve comprises a fluoropolymer.

19. The sleeve of claim 18 wherein the fluoropolymer comprises a polytetafluoroethylene.

* * * * *